United States Patent
Serafini et al.

(10) Patent No.: US 8,426,612 B2
(45) Date of Patent: Apr. 23, 2013

(54) SYNTHESIS OF 3-{[(2R)-1-METHYLPYRROLIDIN-2-YL]METHYL}-5[2-(PHENYLSULFONYL)ETHYL]-1H-INDOLE

(75) Inventors: Siro Serafini, Vicenza (IT); Andrea Castellin, Mestrino (IT); Claudio Dal Santo, Sarego (IT)

(73) Assignee: F.I.S. Fabbrica Italiana Sintetici S.p.A., Alte di Montecchio Maggiore (IT)

( * ) Notice: Subject to any disclaimer, the term of this patent is extended or adjusted under 35 U.S.C. 154(b) by 59 days.

(21) Appl. No.: 12/995,390

(22) PCT Filed: Nov. 9, 2009

(86) PCT No.: PCT/EP2009/064850
§ 371 (c)(1),
(2), (4) Date: Mar. 22, 2011

(87) PCT Pub. No.: WO2010/121673
PCT Pub. Date: Oct. 28, 2010

(65) Prior Publication Data
US 2011/0166364 A1   Jul. 7, 2011

(30) Foreign Application Priority Data
Apr. 22, 2009   (IT) .............................. MI2009A0678

(51) Int. Cl.
C07D 209/04   (2006.01)
(52) U.S. Cl.
USPC ........................................................ 548/468
(58) Field of Classification Search .................. 548/452, 548/468; 514/412
See application file for complete search history.

(56) References Cited

U.S. PATENT DOCUMENTS

| | | | |
|---|---|---|---|
| 5,545,644 A | 8/1996 | Macor et al. | |
| 5,607,951 A * | 3/1997 | Macor et al. | 514/323 |
| 6,927,296 B2 * | 8/2005 | Furlong et al. | 548/465 |
| 7,288,662 B2 | 10/2007 | Ogilvie | |
| 2005/0020663 A1 | 1/2005 | Furlong et al. | |
| 2009/0299077 A1 | 12/2009 | Kansal et al. | |

FOREIGN PATENT DOCUMENTS

| | | |
|---|---|---|
| EP | 0 592 438 B1 | 4/1994 |
| EP | 1 088 817 A2 | 4/2001 |
| WO | WO 92/06973 A1 | 4/1992 |
| WO | WO 96/06842 A1 | 3/1996 |
| WO | WO 02/50063 A1 | 6/2002 |
| WO | WO 2004/089365 A1 | 10/2004 |
| WO | WO 2005/007649 A1 | 1/2005 |
| WO | WO 2008/137134 A2 | 11/2008 |
| WO | WO 2008/150500 A1 | 12/2008 |
| WO | WO 2009142771 * | 5/2009 ................ 548/200 |
| WO | WO 2009/077858 A2 | 6/2009 |
| WO | WO 2009/142771 A2 | 11/2009 |

* cited by examiner

*Primary Examiner* — Samantha Shterengarts
(74) *Attorney, Agent, or Firm* — Dickstein Shapiro LLP

(57) ABSTRACT

The present invention refers to the synthesis of 3-{[(2R)-1-methylpyrrolidin-2-yl]methyl}-5-[2-(phenylsulfonyl)ethyl]-1H-indole, a drug known by the name Eletriptan, or of its salts. In particular, the present invention regards a process for the synthesis of Eletriptan or of its salt, comprising the following steps: a) Salifying the intermediate of Formula (6), using a dicarboxylic acid to obtain a derived salt; b) Optionally, purifying said raw salt obtained according to step a) by solvent crystallization to obtain a purified salt of the intermediate of Formula (6); c) Converting said salt of the intermediate of formula (6) according to step a) or said purified salt according to step b) into an intermediate of formula (10); d) Converting the intermediate of Formula (10) into Eletriptan or its salt.

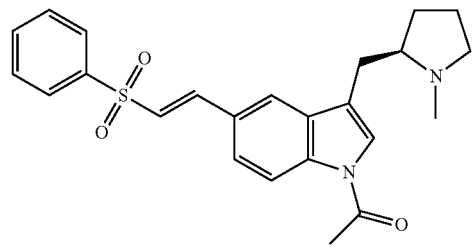

(10)

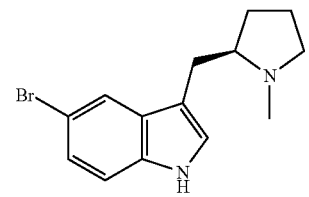

(6)

35 Claims, 7 Drawing Sheets

SYNTHESIS OF 3-{[(2R)-1-METHYLPYRROLIDIN-2-YL]METHYL}-5[2-(PHENYLSULFONYL)ETHYL]-1H-INDOLE

The present invention refers to the synthesis of 3-{[(2R)-1-methylpyrrolidin-2-yl]methyl}-5-[2-(phenylsulfonyl) ethyl]-1H-indole, a drug known by the name Eletriptan, or of its salts.

PRIOR ART

3-{[(2R)-1-methylpyrrolidin-2-yl]methyl}-5-[2-(phenylsulfonyl)ethyl]-1H-indole or Eletriptan, currently available in the market as a hydrobromide salt, is an agonist of the 5-hydroxytryptamine (5-$HT_{1B/1D}$) receptor and it is used for treating migraine.

Various processes of synthesis of such molecule are known, but the one generally used is the synthesis shown in the diagram of FIG. 1, which provides for a Heck reaction (step 4 or 4b) between 5-bromo-3-{[(2R)-1-methylpyrrolidin-2-yl]methyl}-1H-indole and phenyl vinyl sulfone to obtain the 1-(3-{[(2R)-1-methylpyrrolidin-2-yl]methyl}-5-[(E)-2-(phenylsulfonyl)ethenyl]-1H-indole-1-yl)ethanone intermediate.

This reaction uses a palladium-based catalyst which is very sensitive to the impurities present in the reaction environment. It is thus essential that the 5-bromo-3{[(2R)-1-methylpyrrolidin-2-yl]methyl}-1H-indole intermediate be thoroughly purified before being reacted with phenyl vinyl sulfone.

In prior art documents (EP 0 592 438, U.S. Pat. No. 5,545,644 and U.S. Pat. No. 6,100,291) purification of the 5-bromo-3-{[(2R)-1-methylpyrrolidin-2-yl]methyl}-1H-indole intermediate is performed by means of chromatographic column, a process almost exclusively implementable in a laboratory or at a high cost in any case with long processing times alongside being ecologically unadvisable due to the large amount of solvents used.

Furthermore, it is known that the crystallisation of 5-bromo-3-{[(2R)-1-methylpyrrolidin-2-yl]methyl}-1H-indole intermediate (WO 2008/150500 and U.S. Pat. No. 5,545,644) provides a purified intermediate with assay not exceeding 98% (established through the HPLC analysis).

These characteristics of the intermediate are not good enough to guarantee an ideal performance of the subsequent Heck reaction in such a manner to obtain a sufficiently pure product for the subsequent steps.

SUMMARY OF THE INVENTION

Thus, the problem addressed by the present invention is that of providing a process for the synthesis of Eletriptan through a 5-bromoindole intermediate with high purity.

Such a problem is solved through a process as outlined in the attached claims, whose definitions are an integral part of the present description.

BRIEF DESCRIPTION OF THE FIGURES

For exemplification purposes.

DETAILED DESCRIPTION OF THE INVENTION

Figure 1:
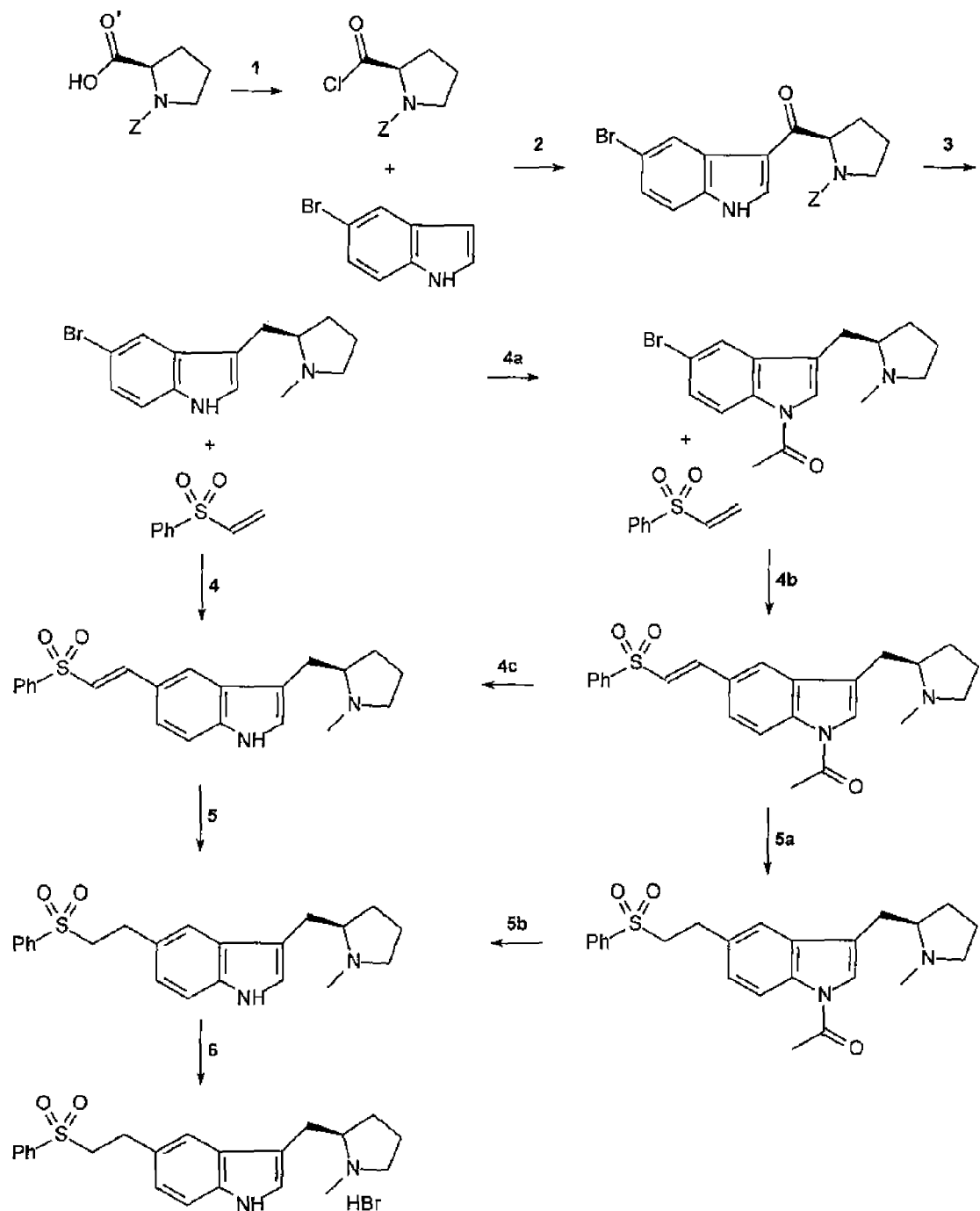
FIG. 1 shows a synthesis diagram of Eletriptan according to the process of the prior art.

The present invention concerns a process for the synthesis of Eletriptan comprising the following steps:
a) Salifying the intermediate of formula 6

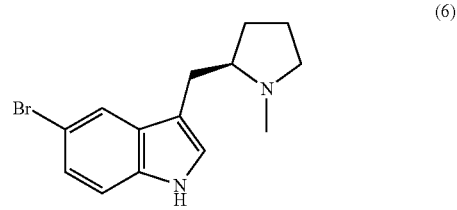 [SMILES: CN1CCC[C@@H]1Cc1c[nH]c2ccc(Br)cc12]

(6)

using a dicarboxylic acid to obtain the corresponding salt;
b) Optionally, purifying said salt obtained according to step a) by solvent crystallization to obtain a purified salt of the intermediate of formula 6;
c) Converting said salt of the intermediate of formula 6 according to step a) or said purified salt according to step b) into an intermediate of formula 10

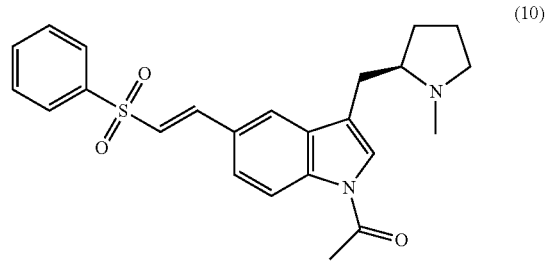 [SMILES: CC(=O)n1cc(C[C@H]2CCCN2C)c2cc(/C=C/S(=O)(=O)c3ccccc3)ccc21]

(10)

d) Converting the intermediate of formula 10 into Eletriptan or its salt.

In an embodiment, steps a) and b) for salifying the intermediate 6 and crystallising the salt thus obtained are carried out in an organic solvent or in a mixture of water and organic solvent miscible in water. Preferably, the organic solvent is an alcohol, more preferably an alcohol selected from among methanol, ethanol, propanol, isopropanol, butanol, isobutanol, tert-Butanol, pentanol. In a particularly preferred embodiment, the alcohol is isopropanol.

When an organic solvent and water mixture is used, the amount of water in the mixture shall preferably be comprised between 10% and 20% in volume.

Preferably, the weight/volume percentage amount of crude intermediate 6 with respect to the solvent varies between 8% and 15% and shall be generally established through an experiment depending on the solvent used.

The dicarboxylic acid is used in stoichiometric amount with respect to the crude intermediate 6 or with a molar excess up to 15%.

Thus obtained is a compound having the formula:

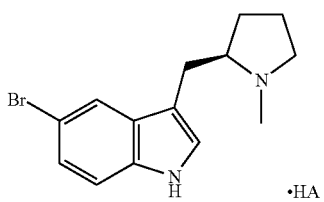 [SMILES: CN1CCC[C@@H]1Cc1c[nH]c2ccc(Br)cc12 ; "·HA"]

wherein HA is a dicarboxylic acid.

The preferred dicarboxylic acid is fumaric acid or oxalic acid, more preferably oxalic acid.

In an embodiment, a solution of intermediate 6 in isopropanol is dropped at room temperature into an isopropanol/water solution into which oxalic acid or fumaric acid is dissolved, in the amounts described previously.

In a different embodiment, oxalic or fumaric acid is added in solid form to a solution of intermediate 6 in ethanol.

After precipitation of the salt of intermediate 6, it is separated, washed using the solvent and dried to obtain the salt of intermediate 6 with purity greater or equal to 99%, determined through the HPLC analysis.

In a particular embodiment, the oxalate salt of the intermediate 6 is recrystallized with water by re-dissolving under heat and reprecipitation, obtaining—after washing and drying—the oxalate salt of the intermediate 6 with purity greater or equal to 99.5%, determined through the HPLC analysis. In such embodiment, the water shall preferably be used in volume/weight amount of intermediate 6 of about 10:1.

In an embodiment, the step c) for converting the salt of intermediate 6 into intermediate 10 is obtained through acylation of indole nitrogen and subsequent Heck condensation of the intermediate thus obtained with phenyl vinyl sulfone. Such process requires, for reacting the two molecules, the presence of tri-o-tolylphosphine and a catalyst Pd(Ac)$_2$.

In an embodiment, the purified salt of intermediate 6 is treated using a basic aqueous solution, for example a sodium or potassium hydroxide aqueous solution, in such a manner to free the base intermediate 6, which is then isolated, dissolved in a suitable solvent, preferably dimethylformamide or analogous dipolar aprotic solvent, and treated with an organic base and an acylating agent. In an embodiment, acetic anhydride and triethylamine are used. Thus, indole nitrogen is acetylated. The reaction may be carried out at a temperature higher than 70° C., preferably about 100° C., over a period of time sufficient to obtain the substantial complete conversion of the free base intermediate 6 to the acetylated product (molecule 8 of FIG. 2), which can be determined through the HPLC analysis.

In a preferred embodiment, the obtained acetylated intermediate 6 is not isolated, but it is added into a solution in suitable solvent, preferably the same solvent used in the acylation process, containing Pd(Ac)$_2$, tri-o-tolylphosphine, phenyl vinyl sulfone and triethylamine.

The molar ratios between said reagents and intermediate 6 are determined by the conventional stoichiometry of the Heck reaction and may for example be about 1:1 phenyl vinyl sulfone/intermediate 6 ratio, about 1:10 tri-o-tolylphosphine/intermediate 6 ratio and 0.5-0.8:10 Pd(Ac)$_2$/intermediate 6 ratio. It is obvious that such molar ratios may vary within given limits, under the supervision of a man skilled in the art, without jeopardising the development of the reaction.

The condensation reaction is preferably carried out at a temperature comprised between 70° C. and the boiling temperature of the solvent for a number of hours sufficient to complete the reaction.

In an embodiment, the step d) of converting the intermediate of formula 10 thus obtained into Eletriptan or its salt comprises:

d1) deacylation reaction of the intermediate of formula 10, and d2) reduction of the double bond C=C adjacent to the sulfonic group, in such a manner to obtain Eletriptan or its salt.

In an embodiment, step d1) is performed by reaction with a base. Preferably, a carbonate of an alkaline or alkaline earth metal or a trialkylamine in an alcohol is used. For example, the reaction may be carried out in the presence of potassium carbonate or dimethylethylamine in methanol.

In an embodiment, step d2) is performed by catalytic hydrogenation, for example in the presence of a catalyst Pd/C.

In an embodiment, the deacylated intermediate 10 is salified with hydrobromic acid before being subjected to catalytic hydrogenation, directly obtaining, after such hydrogenation reaction, Eletriptan hydrobromide.

In a preferred embodiment, step d1) and step d2) are carried out in one step, i.e. without isolating the respective intermediates.

Figure 2:
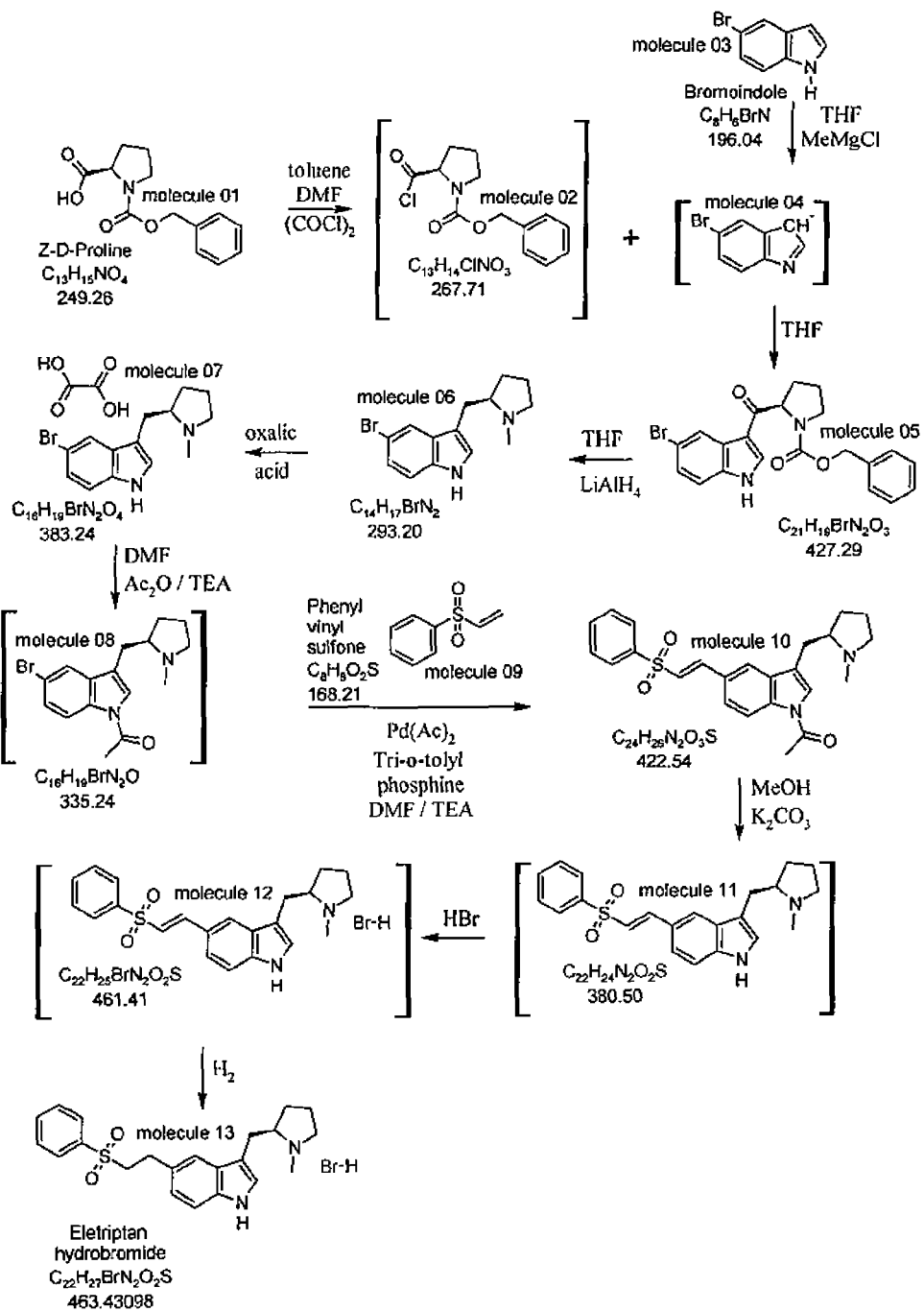
FIG. 2 shows a synthesis diagram of Eletriptan according to a particular embodiment of the invention.
Figure 3:
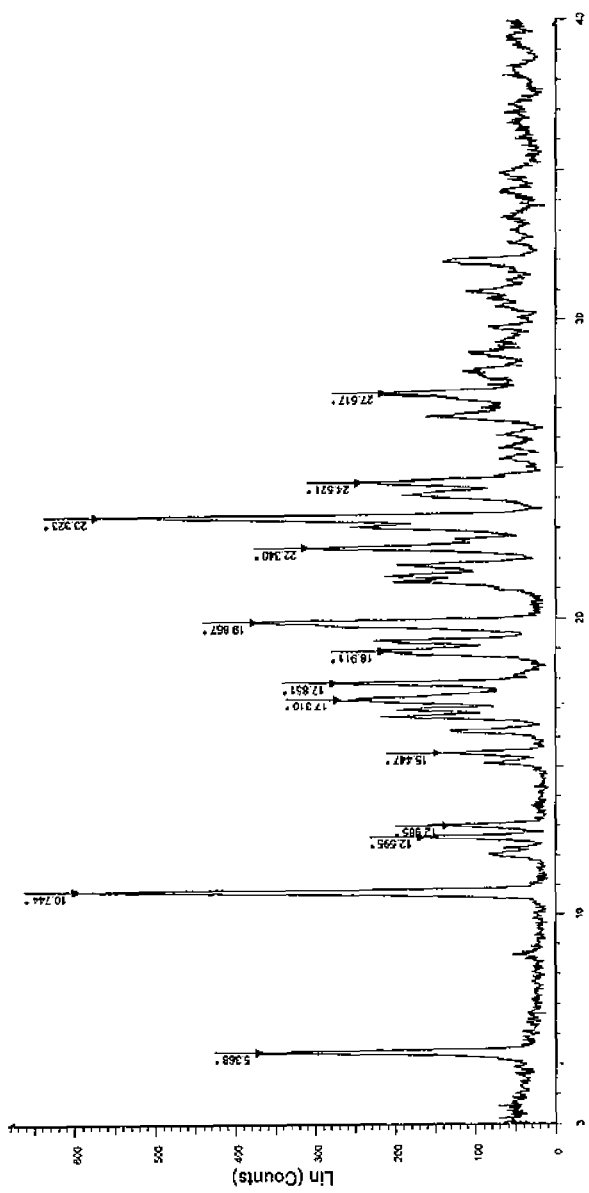
FIG. 3 shows a PXRD patterns of Eletriptan hydrobromide obtained according to the inventive process (Bruker AXS D8 Advance; CuKα, γ=1.5406 Å 40 kV and 40 mA 3 sec/step 0.02°/step)
Figure 4:
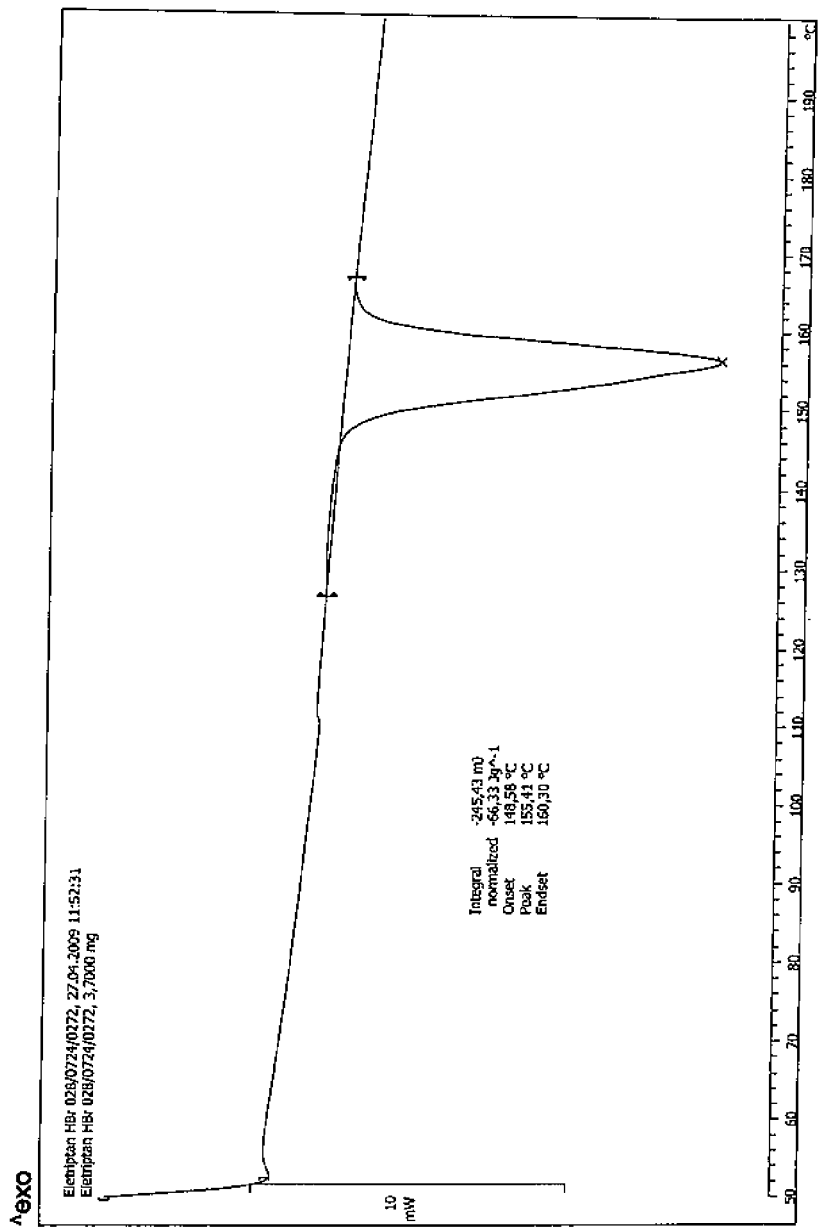
FIG. 4 shows a DSC spectrum of Eletriptan hydrobromide obtained according to the inventive process (Mettler Toledo DSC820; 20° C./min.)
Figure 5:
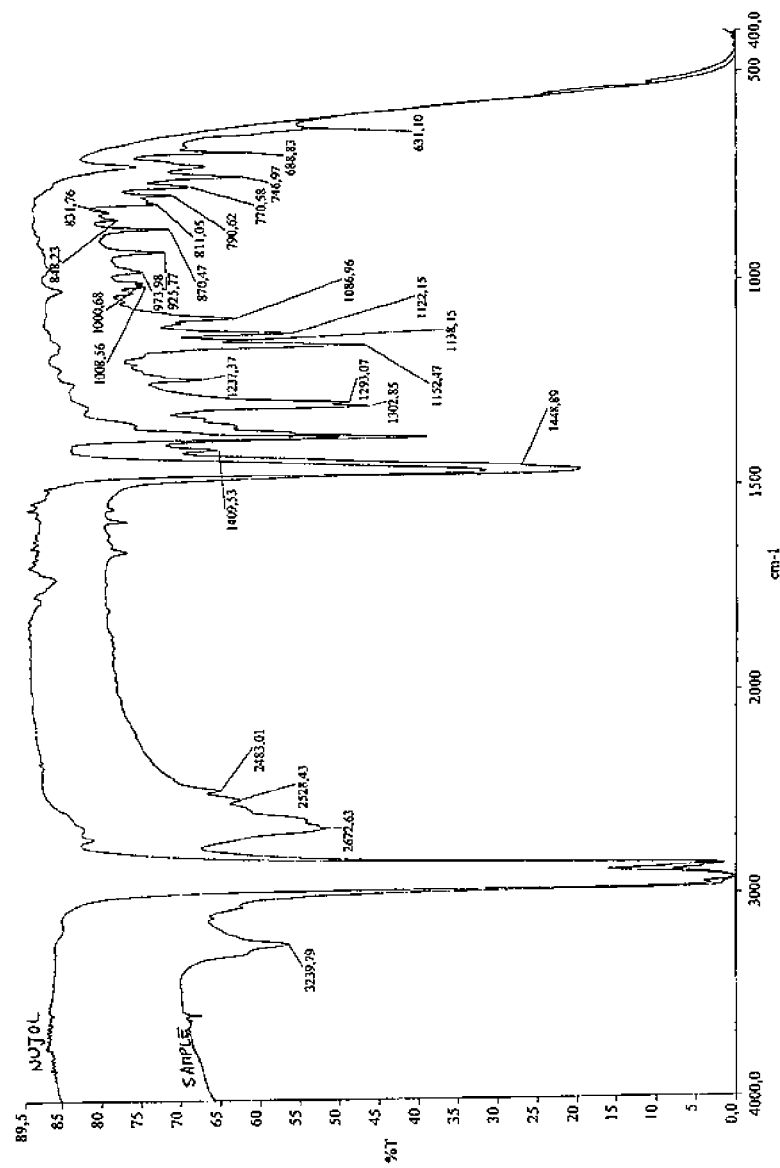
FIG. 5 shows a FT-IR spectrum of Eletriptan hydrobromide obtained according to the inventive process (Perkin-Elmer; nujol mulls)
Figure 6:
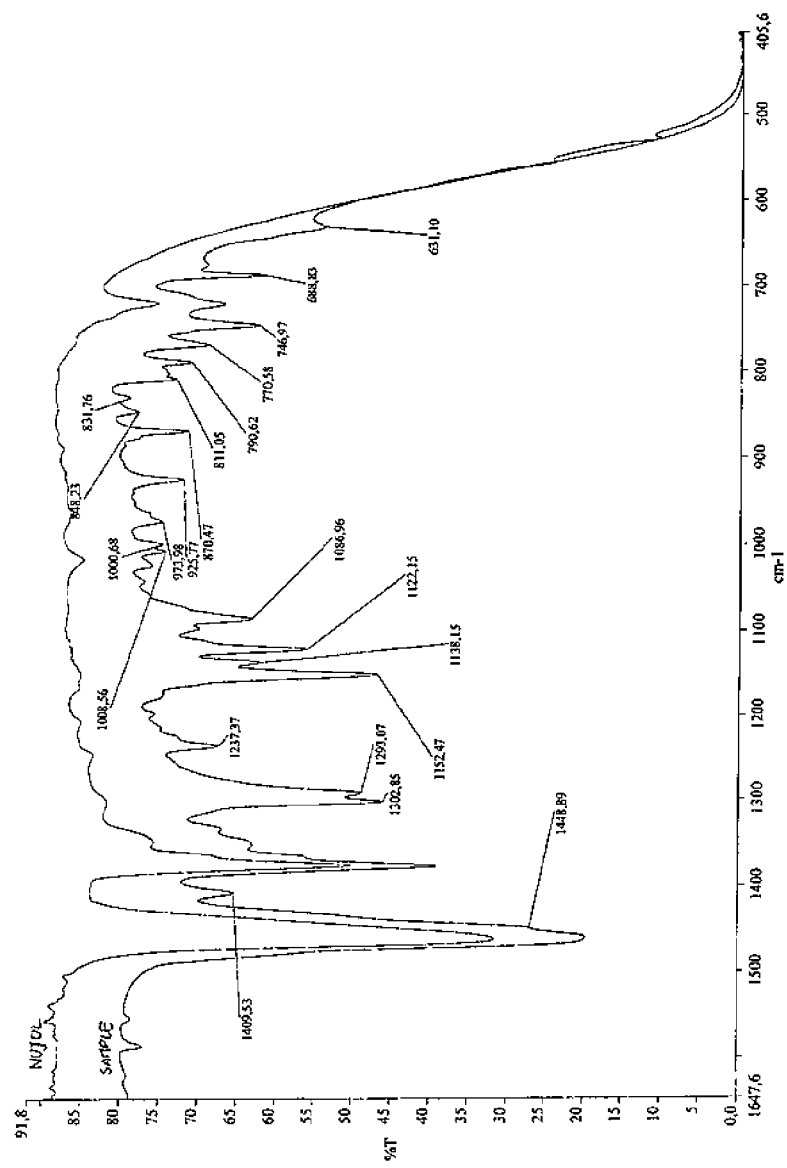
FIG. 6 shows a FT-IR spectrum of Eletriptan hydrobromide obtained according to the inventive process, expanded in a narrower range of wavelengths.
Figure 7:
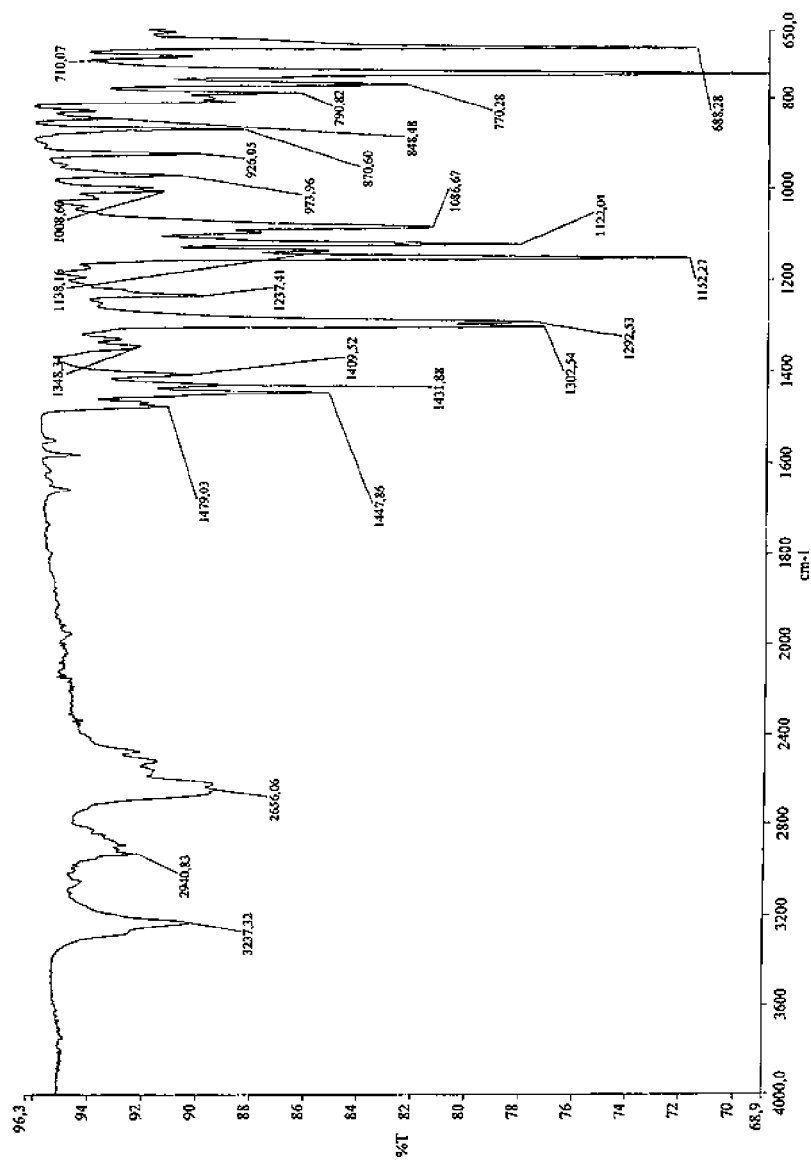
FIG. 7 shows a FT-IR ATR spectrum of Eletriptan hydrobromide obtained according to the inventive process (Perkin-Elmer FT-IR ATR Spectrum 100).

The intermediate of formula 6 may for example be prepared according to the synthesis diagram shown in FIG. 2, which provides for the condensation between R-benzyloxy-carbonyl-proline and 5-bromoindole, after activation of the carboxylic group of proline, and the subsequent removal of the protective benzyloxy-carbonyl group, for example through reduction using lithium aluminium hydride. Still as an example, a detail of the process used is shown in examples 1, 2 and 3.

According to a variation of the process of the invention, also the acetylated intermediate of formula 8 is purified by forming a salt, in particular a fumaric acid or oxalic acid salt, and subsequent crystallisation. The oxalate of the intermediate (8) may be possibly crystallised as described previously regarding the intermediate of formula 6.

According to an embodiment, the process of the invention may skip step a) and b) of salifying and possibly purifying the salt of intermediate 6, replacing the salification of the intermediate 8 and possible purification of the salt thus obtained instead.

Thus obtained is the intermediate of formula:

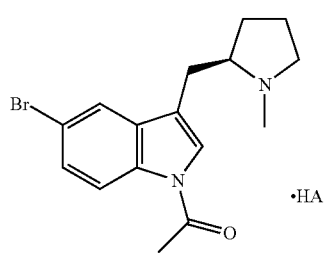 [SMILES: CC(=O)n1cc(C[C@H]2CCCN2C)c2cc(Br)ccc21 ; "·HA"]

wherein HA is a dicarboxylic acid, preferably fumaric acid or oxalic acid.

Therefore, the process shall comprise the following steps:
i) Salifying the intermediate of formula 8

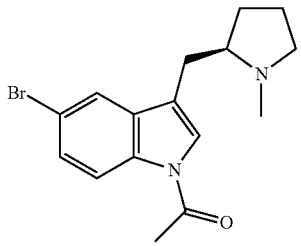

(8)

using a dicarboxylic acid to obtain a derived salt, preferably a salt of fumaric acid or of oxalic acid;
ii) optionally, purifying said salt obtained according to step i) by solvent crystallization to obtain a purified salt of the intermediate of formula 8;
iii) Converting said salt of the intermediate of formula 8 according to step i) or said purified salt according to step ii) into an intermediate of formula 10;

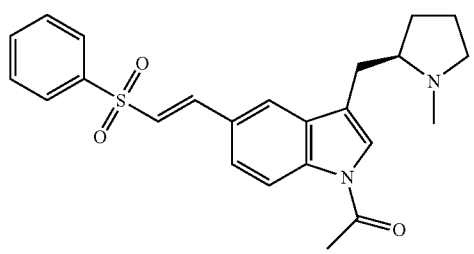

(10)

iv) Converting the intermediate of formula 10 into Eletriptan or its salt.

Salification of the intermediate 8 and possible purification thereof by crystallisation and optional recrystallisation are carried out following the same method described regarding the intermediate of formula 6 and thus shall not be described again.

In one embodiment, the optical purity of Eletriptan can be enhanced up to substantially 100% optical purity by dissolving Eletriptan free base in ethanol and treating it with an amount of oxalic acid ranging from 2% to 6% in weight with respect of the weight of Eletriptan. This procedure allows the precipitation of Eletriptan oxalate (enriched in the S form), while the predominating isomer (R isomer) remains in solution.

The solution of the optically purified Eletriptan free base can then be converted into Eletriptan hydrobromide salt by treating it with hydrobromic acid and crystallizing the resulting salt.

It is thus a further object of the invention a process as defined above, further comprising a step wherein the said Eletriptan free base is treated with an amount from 2% to 6% by weight, with respect of the weight of Eletriptan, of oxalic acid in ethanol, optionally adding activated charcoal, filtering off the solid formed and recovering from the filtrate Eletriptan free base with an optical purity of about 100% and, optionally, converting the said optically purified Eletriptan free base into a hydrobromide salt.

It has been surprisingly found that the process of the invention gives Eletriptan hydrobromide as a monotropic Beta form polymorph which is stable and not hygroscopic. The Beta stable form polymorph of Eletriptan hydrobromide of the invention comprises needle-shaped crystals.

Beta form of Eletriptan hydrobromide is known and has been disclosed in U.S. Pat. No. 6,110,940 in the name of Pfizer. However, in this patent it is reported that Form Beta of Eletriptan hydrobromide is not stable and converts into Form Alpha having a higher melting point. The conversion of Beta form to Alpha form is performed in aqueous acetone. In the later document EP1135381B1, Pfizer confirms the instability of Eletriptan hydrobromide Beta form. In WO2008/137134 Teva Pharmaceuticals USA describes the process of conversion of Beta form to Alpha form by slurrying in organic solvents such as isobutanol, methylacetate, mixtures of THF and water, cyclohexane. Moreover, Alpha form is prepared by simple heating of Beta form at 50° C., under vacuum for 24 hours. In the same document, also a process of conversion of Beta form to Amorphous is described by slurring the Beta form in THF/Water or Ethylacetate/Water or MIBK at 80° C. or Ethylene glycol at 25° C.

It has been determined by the inventors of the present application that monotropic Beta form of Eletriptan hydrobromide prepared according to the above described process is not only very stable, but is also not hygroscopic. Without being bound by any theory, it is believed that the result obtained with the present process is to get an Eletriptan salt which is devoid of a possible, actually unknown undetectable impurity that may be responsible for the instability of the Form Beta described by Pfizer and Teva. The process of preparation of Eletriptan hydrobromide form Beta described by Pfizer and Teva differs from the process of the invention, for example, because the hydrogenation of molecule 11 is performed on the mesylate salt instead of the hydrobromide salt The process of the invention avoids the potential formation of genotoxic impurities related to Methansulphonate esters and the counter ion exchange.

FIGS. 3-7 report the spectral data and the PXRD pattern, DSC curve and FT-IR spectrums of Eletriptan hydrobromide Beta stable form obtained with the inventive process.

Eletriptan hydrobromide Beta stable form as obtained in this invention is characterized by PXRD pattern having peaks at 5.4, 10.7, 12.6, 13.0, 15.4, 17.3, 17.9, 18.9, 19.9, 22.3, 23.3, 24.5, 27.5 degrees 2-Theta; DSC endotherm peak max. at 155° C. (20° C./min.); FT-IR absorption bands in nujol at 3240, 2673, 2528, 1449, 1409, 1302, 1293, 1237, 1152, 1138, 1122, 1086, 973, 926, 870, 811, 791, 771, 747, 689, 631 cm-1; FT-IR ATR absorptions bands at 3237, 2941, 2656, 1479, 1447, 1432, 1409, 1302, 1293, 1237, 1152, 1122, 1087, 973, 926, 870, 790, 770, 745, 688 cm$^{-1}$.

Example 18 below reports some tests that were performed on Eletriptan hydrobromide Beta stable form according to the invention, showing that the product remained stable in all the conditions tested, including also those described in the State of the Art for the conversion of Beta form to other forms.

Example 19 below reports the hygroscopicity test of Eletriptan hydrobromide stable Beta form according to the invention, showing that the product in not hygroscopic.

EXPERIMENTAL PART

Example 1

Molecule 02 in FIG. 2

Benzyl (2R)-2-(chlorocarbonyl)pyrrolidine-1-carboxylate

A mixture composed of 40 mL of toluene and 40 mL of oxalyl chloride was added—in 30 minutes at room temperature—to a solution of 100 g of 1-[(benzyloxy)carbonyl]-D-proline in 200 mL of toluene and 0.5 mL of DMF. After stirring for 2 hours at 20-25° C. the HPLC showed complete conversion and the reaction mixture was concentrated with oil at about 40° C. under vacuum, redissolved to toluene and reconcentrated obtaining 122.1 g of residue. At 20-25° C. the residue was dissolved in 100.00 mL of THF and this solution was used in example 2.

Example 2

Molecule 05 in FIG. 2

Benzyl (2R)-2-[(5-bromo-1H-indole-3-yl)carbonyl]pyrrolidine-1-carboxylate 290.00 mL of methylmagnesium chloride, 3M in THF, were added—in 45 minutes at room temperature—to a solution of 157.3 g of 5-bromo-1H-indole in 1200 mL of MTBE and 400 mL of THF. After short stirring, the solution obtained in example 1 was added rapidly between 3° C. and 17° C. After stirring for 30 minutes at 20° C., 800 mL of 10% aqueous citric acid were slowly added into the reaction mixture obtaining two dissolved phases with pH 3. After filtering the interphase, the lower aqueous phase was separated and discarded. The upper aqueous phase was washed with 200 ml, of 10% citric acid and 200 ml, of water containing sodium chloride, then concentrated to residue under vacuum. After adding 800 mL of MTBE, the resulting suspension was heated at reflux for 60 minutes distilling the water off. The reaction mixture was cooled to 20-25° C. and it was filtered after stirring for 2 hours. The product was washed with 200 mL of MTBE in portions and dried obtaining 109.6 g of the title compound with HPLC assay 99.4%, Karl Fischer 0.47%.

Example 3

Molecule 06 in FIG. 2

5-bromo-3-{[(2R)-1-methylpyrrolidin-2-yl]methyl}-1H-indole

A solution composed of 205 g of benzyl (2R)-2-[(5-bromo-1H-indole-3-yl)carbonyl]pyrrolidine-1-carboxylate in 820 mL of THF was dropped at 60° C. in 30 minutes into a flask containing 307.5 mL of THF and 479.2 mL of 10% LiAlH$_4$. After 3 hours of reflux the control HPLC showed completion of the reaction and the reaction mixture was cooled to 20-25° C. At this temperature a mixture composed of 20.5 mL of H$_2$O and 82 mL of THF was dropped in 15 minutes approximately. Then other 20.5 mL of H$_2$O were added in about 15 minutes, then 41 ml, of 15% NaOH in about 15 minutes, and lastly other 123 mL of H$_2$O in 15 minutes. After stirring for 30 minutes the salts were filtered, washing the cake with 410 mL of isopropanol. The reaction mixture (HPLC assay 65.3%) was concentrated to residue, obtaining 165.3 g of oil. This residue was diluted with 410 mL of isopropanol and used to obtain the oxalate salt.

Example 4

Molecule 07 in FIG. 2

Crude 5-bromo-3-{[(2R)-1-methylpyrrolidin-2-yl]methyl}-1H-indole ethanedioate

Half of the solution obtained in example 3 was dropped in 2 hours under stirring at room temperature in a flask containing 666.2 mL of isopropanol, 153.5 mL of water and 21.6 g of oxalic acid. After stirring for 2 hours at 20-25° C. the crystal obtained was filtered and washed with 103 mL of isopropanol. After drying at 50° C. the product weighed 67.2 g (HPLC purity 96.5%).

Example 5

Molecule 07

Pure 5-bromo-3-{[(2R)-1-methylpyrrolidin-2-yl]methyl}-1H-indole ethanedioate

The crude product obtained in example 4, combined with other crude products for a total of 244 g (HPLC mean assay 96.4%), was dissolved at reflux in 2440 mL of water, treated under heat with 12.2 g of activated chaecoal, filtered under heat and cooled to 0° C. in about 40 minutes. After stirring for 1 hour at 0° C. the crystalline product was filtered and washed with 244 mL of water to obtain, after drying, 199 g of oxalate molecule 7 having HPLC assay 99.5%, Karl Fischer 0.14%.

Example 6

Molecule 07

5-bromo-3-{[(2R)-1-methylpyrrolidin-2-yl]methyl}-1H-indole etanedioato

A solution of 10 g of 5-bromo-3-{[(2R)-1-methylpyrrolidin-2-yl]methyl}-1H-indole (like oil containing traces of toluene, HPLC purity 98.3%) in 20 mL of isopropanol, was dropped for about 2 hours at 20-25° C. into a solution composed of 65 mL of isopropanol, 15 mL of water and 3.4 g of anhydrous oxalic acid. After stirring for 2 hours at 20-25° C. the reaction mixture was filtered and the crystalline product dried at 80° C. obtaining 8.72 g (Karl Fischer 0.09%, HPLC purity 99.6%). The product (oxalate molecule 7) has a 192.5° C. (DSC 10°/min) melting point, $^1$H-NMR (DMSO-d$_6$) spectrum: δ 11.30 (br s, 1H), 7.81 (br d, 1H), 7.37-7.33 (m, 2H), 7.21 (dd, j=1.9 Hz and 8.7 Hz, 1H), 3.64-3.48 (m, 2H), 3.32 (dd, j=14 Hz and 4.9 Hz, 1H), 3.11-3.00 (m, 1H), 2.96-2.85 (m, 1H), 2.83 (s, 3H), 2.04-1.84 (m, 3H), 1.80-1.67 (m, 1H) and a titre with NaOH corresponding to a 1:1 stoichiometry with oxalic acid.

Example 7

Molecule 07 Fumarate 5-bromo-3-{[(2S)-1-methylpyrrolidin-2-yl]methyl}-1H-indole (2E) but-2-enedioate 3.46 g of fumaric acid were added to a solution of 8.75 g of crude 5-bromo-3-{[(2S)-1-methylpyrrolidin-2-yl]methyl}-1H-indole (HPLC assay 64.9%) in 43.75 mL of ethanol. After stirring for 2 hours the reaction mixture was filtered washing with mL of ethanol/heptane in a 1/1 ratio and the crystal was dried in oven under vacuum until a constant weight of 7.1 g (HPLC purity 91.7%) was obtained.

Example 8

Molecule 07 Fumarate 5-bromo-3-{[(2R)-1-methylpyrrolidin-2-yl]methyl}-1H-indole (2E) but-2-enedioate A solution of 10 g of 5-bromo-3-{[(2R)-1-methylpyrrolidin-2-yl]methyl}-1H-indole (as oil containing traces of toluene, HPLC purity 98.3%) in 20 ml, of isopropanol, were dropped in about 2 hours at 30-35° C. into a solution composed of 65 ml, of isopropanol, 15 mL of water and 4.4 g of anhydrous fumaric acid. After stirring for 2 hours at 20-25° C. the reaction mixture was filtered and the crystalline product dried at 80° C. obtaining 7.12 g (Karl Fischer 0.08%, HPLC purity 99.4%). By cooling the mother liquors at −15° C., 1.23 g (Karl Fischer 0.17%, HPLC purity 99.0%) were further obtained. The product (molecule 7 fumarate) has a 199.4° C. (DSC 10°/min) melting point, $^1$H-NMR (DMSO-$d_6$) spectrum: δ 11.18 (br s, 1H), 7.75 (d, j=1.9 Hz, 1H), 7.3 (d, j=8.6 Hz, 1H) 7.3 (d, j=2.3 Hz, 1H), 7.18 (dd, j=1.9 Hz and 8.6 Hz, 1H), 6.54 (s, 2H), 3.41-3.31 (m, 1H), 3.21 (dd, j=14 Hz and 4.5 Hz, 1H), 3.13-3.02 (m, 1H), 2.8-2.65 (m, 2H), 2.62 (s, 3H), 1.92-1.72 (m, 3H), 1.70-1.56 (m, 1H) and a titre with NaOH corresponding to a 1:1 stoichiometry with fumaric acid.

Example 9

Molecule 10

1-(3-{[(2R)-1-methylpyrrolidin-2-yl]methyl}-5-[(E)-2-(phenylsulfonyl)ethenyl]-1H-indole-1-yl)ethanone A mixture of 570 grams of 5-bromo-3-{[(2R)-1-methylpyrrolidin-2-yl]methyl}-1H-indole ethanedioate, 4360 mL of toluene, 4360 mL of water and 436 ml, of 50% in weight aqueous KOH was loaded into a reactor and stirred for 15 minutes at 21-25° C., then after decanting the lower aqueous phase was discarded and the organic phase washed with 436 mL of water and concentrated to residue, obtaining 512 g of oil. This residue was dissolved in 349 mL of dimethylformamide, then 289 mL of triethylamine and 196 mL of acetic anhydride were added. The reaction mixture was heated at 100° C. for 4 hours under stirring, then an HPLC control showed complete conversion to acetylated compound. 959 mL of degassed DMF, 20.7 g of palladium acetate and 56.7 g of tri-o-tolylphosphine were added into another flask. After stirring for 30 minutes, 313 g of phenyl vinyl sulfone, 436 mL of triethylamine and the solution acetylated compound prepared previously were added. After 5 hours at reflux (about 115° C.) and subsequent cooling to 50° C., the reaction mixture was added into a reactor containing 2550 mL of isopropyl acetate and 436 mL of water at 55° C. 44 g of activated charcoal were added and, after stirring for 1 hour, the reaction mixture was filtered on cartridge, washing with 939 mL of isopropyl acetate. Other 500 mL of isopropyl acetate were used to wash the cartridge and then distilled under vacuum to return to volume. 3489 mL of water were added—between 20 and 23° C.—in 1 hour, leaving under stirring for about 16 hours. Then the reaction mixture was filtered, the crude product was washed with 1310 mL of water and dried at 35° C. until the weight of 460.3 g (Karl Fischer 6.9%, HPLC purity 97.0%) was reached.

Example 10

Molecule 08 Oxalate 1-(5-bromo-3-{[(2R)-1-methylpyrrolidin-2-yl]methyl}-1H-indole-1-yl)ethanone ethanedioate The acetylated compound obtained in a manner similar to that of example 9 (14.2 g of crude oil, pure at 93% approximately, containing toluene) was dissolved in 14.2 mL of ethanol and dropped into a solution of 3.79 g of anhydrous oxalic acid in 47.3 mL of ethanol. After crystallisation the product was filtered, washed with ethanol and dried obtaining 9.0 g of 1-(5-bromo-3-{[(2R)-1-methylpyrrolidin-2-yl]methyl}-1H-indole-1-yl)ethanone ethanedioate, 99.5% pure. The product (oxalate molecule 8) has a 150° C. (DSC 10°/min) melting point, $^1$H-NMR (DMSO-$d_6$) spectrum: δ 8.27 (d, j=8.8 Hz, 1H), 7.93 (br d, j=1.9 Hz, 1H), 7.89 (s, 1H), 7.51 (dd, j=1.9 Hz and 8.8 Hz, 1H), 3.67-3.53 (m, 2H), 3.33 (br dd, j=13.9 Hz and 4.7 Hz, 1H), 3.12-3.00 (m, 1H), 2.98-2.88 (m, 1H), 2.86 (s, 3H), 2.64 (s, 3H), 2.12-1.86 (m, 3H), 1.82-1.69 (m, 1H) and a titre with NaOH corresponding to a 1:1 stoichiometry with oxalic acid.

Example 11

Molecule 10

1-{[(2R)-1-methylpyrrolidin-2-yl]methyl}-5-[(E)-2-(phenylsulfonyl)ethenyl]-1H-indole-1-yl)ethanone For purification, 160 g of the product obtained in example 9 were dissolved in acetone and loaded into a column filled with 400 g of silica gel, eluting with 4 liters of acetone/triethylamine in 99:1 ratio. After concentrating the fractions containing the product, 143.3 g of product were obtained. Of these, 130 g were dissolved in 390 mL of acetone and reprecipitated slowly adding 520 mL of water. After 2 hours at 20-25° C. the product was filtered and dried at 35° C. until a constant weight was reached, obtaining 134.8 g (Karl Fischer 0.54%, HPLC purity 99.1%).

Example 12

Molecule 10

1-(3-{[(2R)-1-methylpyrrolidin-2-yl]methyl}-5-[(E)-2-(phenylsulfonyl)ethenyl]-1H-indole-1-yl)ethanone For purification, 160 g of the product obtained in example 9 were dissolved in acetone and loaded into a column filled with 400 g of silica gel, eluting with 4 liters of acetone/triethylamine in a 99:1 ratio. After concentrating the fractions containing the product, 142.6 g of product were obtained. Of these, 120 g were dissolved into 623 mL of toluene and, after treatment with 5 g of decolorizing charcoal, reprecipitated by slowly adding 623 mL of heptane. After the weekend at 20-25° C., the product was filtered and dried at 35° C. until a constant weight is reached, obtaining 105.6 g (Karl Fischer 0.27%, HPLC purity 98.6%).

Example 13

Molecule 10

1-(3-{[(2R)-1-methylpyrrolidin-2-yl]methyl}-5-[(E)-2-(phenylsulfonyl)ethenyl]-1H-indole-1-yl)ethanone For purification, 121 g of crude product, obtained in a manner similar to example 9, were diluted with 484 mL of toluene and 484 mL of heptane. After treatment and subsequent hot filtration with 6 g of decolorizing charcoal, 484 mL of heptane were added—at 20-25° C.—in 1 hour. After 2 hours at 20-25° C., the product was filtered and dried at 35° C. until constant weight was reached, obtaining 110.2 g (Karl Fischer 0.23%, HPLC purity 99.0%).

Example 14

Molecule 13

3-{[(2R)-1-methylpyrrolidin-2-yl]methyl}-5-[2-(phenylsulfonyl)ethyl]-1H-indole hydrobromide (Eletriptan Hydrobromide)

A solution composed of 2.8 g of potassium carbonate in 5.6 mL of water were dropped into a flask containing a mixture of 55.6 g of 1-(3-{[(2R)-1-methylpyrrolidin-2-yl]methyl}-5-[(E)-2-(phenylsulfonyl)ethenyl]-1H-indole-1-yl)ethanone in 222 mL of methanol. After 20 minutes the HPLC showed quantitative conversion to 3-{[(2R)-1-methylpyrrolidin-2-yl]methyl}-5-[(E)-2-(phenylsulfonyl)ethenyl]-1H-indole, thus after adding 333 ml, of water the solvent was evaporated under vacuum until a residue of 277 mL was reached and 278 mL of methyltetrahydrofuran were added under stirring to form two clear phases. After separation, the aqueous phase was re-extracted with 83 mL of methyltetrahydrofuran and the recombined organic phases were washed with 138 mL of water. After concentration to residue (obtaining 50.4 g of oil, HPLC purity 99.1%), 350 mL of acetone and 100 ml, of water were added. After treatment with activated charcoal, 10 mL of 62% aqueous hydrobromic acid were slowly added up to a 1.5 pH. After treatment with charcoal, the reaction mixture was subjected to hydrogenation in an autoclave at 20° C. and then at 50° C. using 18.5 g of 5% palladium on carbon—50% humidity—added in two portions, as a catalyst. Upon completion of the reaction, after filtering the catalyst the reaction mixture was concentrated to residue and diluted with 500 mL of acetone under stirring for about 16 hours. The product was filtered and dried at 40° C. until constant weight was reached, obtaining 38.5 g (Karl Fischer 0.19%, HPLC purity 99.6%).

Example 15

Molecule 13

3-{[(2R)-1-methylpyrrolidin-2-yl]methyl}-5-[2-(phenylsulfonyl)ethyl]-1H-indole hydrobromide (Eletriptan Hydrobromide)

The preparation of example 14 has been repeated by hydrolising the acetyl derivative (molecule 10) with an organic amine.

3 g of molecule 10 have been dissolved in 12 ml of methanol, then 1.58 ml of dimethylethylamine were added dropwise. After 1 hr under stirring at room temperature and 5 hr at reflux, the reaction mixture was concentrated and redissolved in 15 ml of methanol and this operation was again repeated. The residue was dissolved in 27 ml of methanol and 0.54 ml of a solution of 60% HBr in water were added dropwise. After 2 hr the crystallised product was filtered and washed with isopropanol, to give 2.3 g of molecule 12 having a purity of 99.8%. This intermediate can be subjected to hydrogenation as described in example 14.

Example 16

Molecule 13

3-{[(2R)-1-methylpyrrolidin-2-yl]methyl}-5-[2-(phenylsulfonyl)ethyl]-1H-indole hydrobromide (Eletriptan Hydrobromide)

A solution of 2.5 g of anhydrous potassium carbonate in 5 ml of water was added dropwise into a solution of 50 g of molecule 10 in 200 ml of methanol, during 15 minutes. The reaction was conducted under stirring at 20-25° C. and was monitored by HPLC. When the starting compound was present in amount less than 0.5%, the reaction mixture was brought to pH 8 by adding 5 ml of acetic acid and treated with decolorizing charcoal. After evaporation of most of the solvent, 300 ml of water were added and the solvent was evaporated again to a residue of 250 mL. Methyltetrahydrofuran (250 ml) was added and the mixture was brought to pH approx. 12 with 6 ml of 30% NaOH aqueous solution. The phases were separated and the aqueous phase was extracted with 75 ml of methyltetrahydrofuran. The organic phases were collected and washed with water. The resulting organic phase was concentrated under vacuum at 50° C., obtaining 46.8 g of molecule 11 as an oil.

This oil was dissolved in 450 ml of methanol and treated dropwise with 9 ml of 62% aqueous HBr until pH 1.5 was reached, obtaining molecule 12. After 1 hr under stirring at 20-25° C., 16.25 g of 5% Pd/C (50% wet) were added to the suspension, and the reaction mixture was hydrogenated in autoclave at 5 atm of hydrogen and 20-25° C. The reaction was monitored by HPLC until the starting product was present in amount less than 0.5%, then the catalyst was filtered off and the mixture was concentrated under vacuum to an oil. The residue was dissolved in 135 ml of isopropanol and again concentrated under vacuum to an oil. The residue was diluted with 450 ml of isopropanol and heated at reflux for 30 minutes. Further 200 ml of isopropanol were added, the mixture was filtered on activated carbon and concentrated to the initial volume.

The temperature was brought slowly to 20-25° C., then the suspension was stirred at 20-25° C. and filtered, washing with 45 ml of isopropanol. The solid was dried to give 37.9 g of raw molecule 13, yield 69.1% and HPLC purity 99.7%.

Raw molecule 13 (70 g) was diluted with 168 ml of acetone and 672 ml of isopropanol. The resulting mixture was heated at reflux until dissolution, treated with decolorizing charcoal and the solvent was removed. The residue was diluted with 154 ml of acetone and 616 ml of isopropanol, then it was cooled in 1 hour to 10° C. and stirred for at least 2 hr at 10° C. The solid was filtered and washed with 140 ml of isopropanol, then dried to give 61.6 g of Eletriptan hydrobromide, crystallization yield 88%, HPLC purity 99.7%.

Example 17

Molecule 13

Optical purification of 3-{[(2R)-1-methylpyrrolidin-2-yl]methyl}-5-[2-(phenylsulfonyl)ethyl]-1H-indole (Eletriptan)

71 g of Eletriptan hydrobromide (having an enantiomeric purity of 91% R form and 9% S form) are treated with 355 mL of $CH_2Cl_2$ and approx. 190 mL of NaOH 2% in water. The pH is adjusted to 12, then the aqueous phase is separated and extracted with 106 mL of $CH_2Cl_2$. The two organic phases are combined and washed with 106 mL of $H_2O$. After treatment with decolorizing charcoal and sodium sulfate, the solvent is removed by rotary evaporation and 56.3 g of eletriptan free base as an oil are obtained.

53 g of Eletriptan free base having an enantiomeric purity of 91% R form and 9% S form, were dissolved in 530 ml of ethanol and a solution of 2.5 g of anhydrous oxalic acid in 265 ml of ethanol was added dropwise. The reaction mixture was kept at room temperature overnight, then it was filtered and the solid (Eletriptan oxalate enriched in S-enantiomer)) was discharged. The filtrate was treated with 2 g of carbon, filtered and concentrated to dryness giving 31.3 g of Eletriptan free base, 100% R form.

Optionally, the product so obtained is dissolved in 300 ml of methylene chloride and 100 ml of water and the pH is brought to pH 12 by adding 10% aqueous KOH. The aqueous phase is separated, while the organic phase is concentrated to give a residue of 29.6 g. This residue is dissolved in 592 ml of isopropanol and treated with 5.8 ml of 62% aqueous hydrobromic acid to reach a final pH 2.5. The hydrobromide salt crystallizes. After 2 hr under stirring, it is filtered and washed with 60 ml of isopropanol. After drying, 29.8 g of Eletriptan hydrobromide, 100% R form, are obtained.

Example 18

Stability Tests of Eletriptan Hydrobromide Beta Form Polymorph

Eletriptan hydrobromide Beta form obtained according to the inventive process has been subject to a series of experiments to assess its stability against the conversion into Form Alpha of higher melting point or in amorphous.

These experiments have been performed in various solvents and at various temperature and time conditions. In all the experiments, Eletriptan hydrobromide Form Beta did not convert into Form A, amorphous or other crystalline forms or in any hydrated form. The DSC trace is the same for all the product prepared according to Example 18 and is the same of that of Beta polymorph.

The results are reported in the following table.

| Eletriptan·HBr (mg) | Solvent 1 (ml) | Solvent 2 (ml) | Temperature ° C. | Time hr |
|---|---|---|---|---|
| 250 | t-BuOH (18) | — | Δ/RT | 48 |
| 250 | t-BuOH (33) | Water (0.525) | Δ/RT | 48 |
| 250 | MEK (2.5) | Water (0.075) | RT | overnight |
| 250 | Cyclohex. (2.5) | — | 80° C. | 6 |
| 250 | Heptanes (2.5) | — | 80° C. | 6 |
| 250 | Xylene (2.5) | — | 80° C. | 6 |
| 250 | iPrOAc (2.5) | — | 80° C. | 6 |
| 250 | tBuOAc (2.5) | — | 80° C. | 6 |
| 250 | nBuOAc (2.5) | — | 80° C. | 6 |
| 250 | i-BuOH (2.5) | — | 80° C. | 6 |
| 250 | Me/i-Bu carbinol (2.5) | — | 80° C. | 6 |
| 250 | Diethyl carbonate (2.5) | — | 80° C. | 6 |
| 250 | Dimethyl carbonate (2.5) | — | 80° C. | 6 |
| 250 | CH2Cl2 (2.5) | — | 80/RT | Overnight |
| 250 | MeTHF (2.5) | — | 80/RT | 5 |
| 250 | Me/i-BuK (2.5) | — | 80/RT | 5 |
| 250 | DEK (2.5) | — | 80/RT | 5 |
| 250 | PhCl (2.5) | — | 80/RT | 5 |
| 100 | Water (2) | — | Δ/RT | Overnight |
| 1000 | Acetone (2.5) | Water (0.125) | RT/Δ | 48 |
| 250 | — | — | 80° C. | Overnight |
| 250 | Water-saturated atm. | — | RT | 48 |
| 100 | Sonication | — | RT | 5 |

In addition, the same experiments described in U.S. Pat. No. 6,110,940 (example 2) and WO2008/137134 (examples 16, 17, 18, 19) to convert Eletriptan Beta form to Alpha form and those described in WO2008/137134 (examples 2, 7, 8, 12 and 13) to convert Eletriptan Beta form to amorphous were carried out on Eletriptan Hydrobromide form Beta of invention, applying exactly the same conditions. All these trials provided only Eletriptan hydrobromide form Beta. Furthermore, all trial performed during a DSC study directed to convert Eletriptan hydrobromide Beta form of invention to other forms by means of heating/cooling cycles provided always Form Beta. There results confirms the stability of Eletriptan hydrobromide Beta form of invention and his different behaviour in comparison with the same form described in the State of the Art.

Example 19

Hygroscopicity Test of Eletriptan Hydrobromide Form Beta Polymorph

Eletriptan hydrobromide Beta stable form obtained according to the inventive process has been subject to the hygroscopicity test as described in the European Pharmacopoeia 5.0 (25° C., 80% rel. humidity, 24 h). Eletriptan hydrobromide results not hygroscopic (0.1%).

The invention claimed is:

1. Process for the synthesis of Eletriptan or of its salt, comprising the following steps:
   a) salifying the intermediate of formula (6)

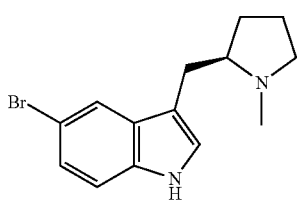

(6)

using a dicarboxylic acid to obtain a derived salt;
   b) optionally, purifying said salt obtained according to step a) by solvent crystallization to obtain a purified salt of the intermediate of formula (6);
   c) converting said salt of the intermediate of formula (6) according to step a) or said purified salt according to step b) into an intermediate of formula (10)

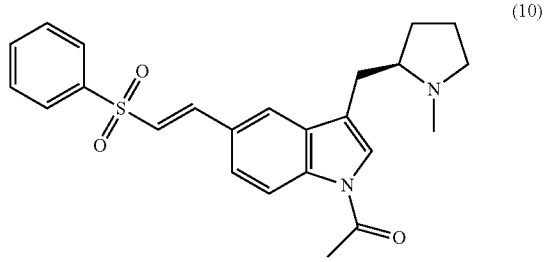 [SMILES: CC(=O)n1cc(C[C@H]2CCCN2C)c2cc(/C=C/S(=O)(=O)c3ccccc3)ccc21]

d) converting the intermediate of formula (10) into Eletriptan or its salt.

2. Process according to claim 1, wherein said steps a) and b) for salifying the intermediate (6) and crystallising the salt thus obtained are carried out in an organic solvent or in a mixture of water and organic solvent mixable in water.

3. Process according to claim 2, wherein said organic solvent is an alcohol.

4. Process according to claim 3, wherein said alcohol is selected from among methanol, ethanol, propanol, isopropanol, butanol, isobutanol, tert-Butanol, pentanol.

5. Process according to claim 2, wherein, when an organic solvent and water mixture is used, the amount of water in the mixture shall be comprised between 10% and 20% in volume.

6. Process according to claim 2, wherein the weight/volume percentage amount of the crude intermediate (6) with respect to the solvent varies between 8% and 15%.

7. Process according to claim 1, wherein said dicarboxylic acid is used in stoichiometric amounts with respect to the crude intermediate (6) or with a molar excess up to 15%.

8. Process according to claim 1, wherein said dicarboxylic acid is fumaric acid or oxalic acid.

9. Process according to claim 1, wherein, in said steps a) and b), a solution of intermediate (6) in isopropanol is dropped at room temperature into an isopropanol/water solution into which oxalic acid or fumaric acid is dissolved.

10. Process according to claim 1, wherein, in said steps a) and b), oxalic or fumaric acid is added in solid form to a solution of intermediate (6) in ethanol.

11. Process according to claim 1, wherein said dicarboxylic acid is oxalic acid and wherein the oxalate salt of the intermediate (6) is recrystallised by water through redissolution under heat and reprecipitation.

12. Process according to claim 11, wherein water is used in a volume/weight amount of intermediate (6) of about 10:1.

13. Process according to claim 1, wherein said purified salt of intermediate (6) has a purity greater or equal to 99% or greater or equal to 99.5%, determined through the HPLC method.

14. Process according to claim 1, wherein said step c) of converting the salt of intermediate (6) obtained according to step a) or step b) into said intermediate (10) is obtained through acylation of indolic nitrogen and subsequent Heck condensation of the intermediate thus obtained with phenyl vinyl sulfone in presence of tri-o-tolylphosphine and a catalyst Pd(Ac)$_2$.

15. Process according to claim 14, wherein said salt of intermediate (6) is previously treated with a basic aqueous solution in such a manner to free the intermediate (6) free base and wherein said intermediate (6) free base is isolated, dissolved into a suitable solvent and added with an organic base and an acylating agent.

16. Process according to claim 15, wherein said solvent is dimethylformamide or another dipolar aprotic solvent, said acylating agent is acetic anhydride and said base is triethylamine and wherein the reaction is performed at a temperature exceeding 70° C., or about 100° C., for a period of time sufficient to obtain the substantial complete conversion of the free base intermediate (6) to the acetylated product, determinable through the HPLC method.

17. Process according to claim 14, wherein said acetylated intermediate (6) is converted into oxalic acid salt and purified by crystallisation and possible recrystallisation by means of suitable solvents.

18. Process according to claim 14, wherein said acetylated intermediate (6) is added without isolation in a solution containing Pd(Ac)$_2$, tri-o-tolylphosphine, phenyl vinyl sulfone and triethylamine.

19. Process according to claim 18, wherein the molar ratios between said reagents and intermediate (6) are about 1:1 regarding phenyl vinyl sulfone, about 1:10 regarding tri-o-tolylphosphine and 0.5-0.8:10 regarding Pd(Ac)$_2$.

20. Process according to claim 18, wherein said condensation reaction is performed at a temperature comprised between 70° C. and the boiling temperature of the solvent for a number of hours sufficient to complete the reaction.

21. Process according to claim 1, wherein said step d) of converting the intermediate of formula (10) into Eletriptan or its salt comprises:
    d1) deacylation reaction of the intermediate of formula (10), and
    d2) reduction of the double bond C=C adjacent to the sulfonic group, in such a manner to obtain Eletriptan or its salt.

22. Process according to claim 21, wherein said step d1) is performed in presence of potassium carbonate in methanol or in the presence of a trialkylamine.

23. Process according to claim 21, wherein said step d2) is performed by catalytic hydrogenation.

24. Process according to claim 21, wherein said deacylated intermediate (10) is salified with hydrobromic acid before being subjected to catalytic hydrogenation, directly obtaining, after such hydrogenation reaction, Eletriptan hydrobromide.

25. Process according to claim 21, wherein said step d1) and said step d2) are performed in one step, without isolating the respective intermediates.

26. Process according to claim 15, further comprising a step wherein the said Eletriptan free base is treated with an amount from 2% to 6% by weight, with respect of the weight of Eletriptan, of oxalic acid in ethanol, filtering off the solid formed and recovering from the filtrate Eletriptan free base with an optical purity of about 100%.

27. Process according to claim 26, further comprising a step of treating the optically purified Eletriptan free base with hydrobromic acid to give optically purified Eletriptan hydrobromide salt.

28. Compound of formula:

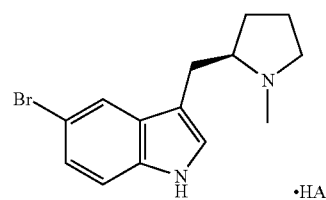 [SMILES: CN1CCC[C@@H]1Cc1c[nH]c2ccc(Br)cc12 ; "·HA"]

wherein HA is a dicarboxylic acid.

29. Compound according to claim 28, wherein HA is fumaric acid or oxalic acid.

30. Process for the synthesis of Eletriptan or of its salt, comprising the following steps:
 i) salifying the intermediate of formula (8)

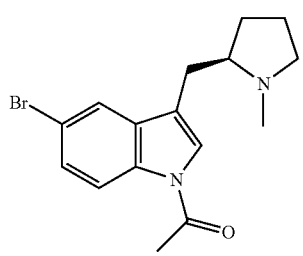

(8)

using a dicarboxylic acid to obtain a derived salt, preferably salt with fumaric acid or oxalic acid;
 ii) optionally, purifying said salt obtained according to step i) by solvent crystallization to obtain a purified salt of the intermediate of formula (8);
 iii) converting said salt of the intermediate of formula (8) according to step i) or said purified salt according to step ii) into an intermediate of formula (10);

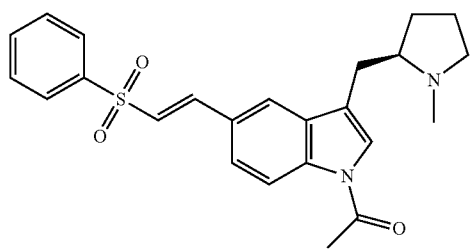

(10)

iv) converting the intermediate of formula (10) into Eletriptan or its salt, wherein said steps i) and ii) are performed as described regarding the intermediate (6) in claim 1.

31. Compound of formula:

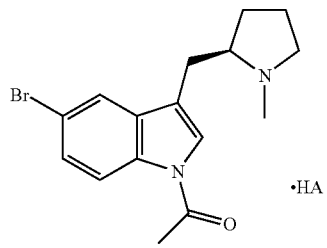 [SMILES: CC(=O)n1cc(C[C@H]2CCCN2C)c2cc(Br)ccc21 ; "·HA"]

·HA wherein HA is a dicarboxylic acid.

32. A beta-stable form of eletriptan hydrobromide of formula

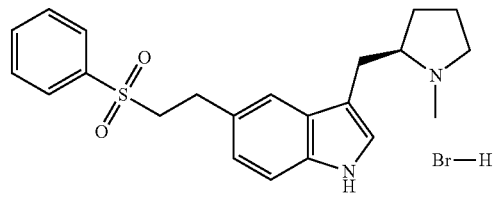

Br—H wherein said beta-stable form of Eletriptan hydrobromide does not convert into an Alpha form of higher melting point.

33. Eletriptan hydrobromide according to claim 32, which is not hygroscopic.

34. Eletriptan hydrobromide according to claim 32, which comprises needle-shaped crystals.

35. Eletriptan hydrobromide according to claim 32, characterized by PXRD pattern having peaks at 5.4, 10.7, 12.6, 13.0, 15.4, 17.3, 17.9, 18.9, 19.9, 22.3, 23.3, 24.5, 27.5 degrees 2-Theta; and/or DSC endotherm peak max, at 155° C. (20° C./min.); and/or FT-IR absorption bands in nujol at 3240, 2673, 2528, 1449, 1409, 1302, 1293, 1237, 1152, 1138, 1122, 1086, 973, 926, 870, 811, 791, 771, 747, 689, 631 cm-1; and/or FT-IR ATR absorptions bands at 3237, 2941, 2656, 1479, 1447, 1432, 1409, 1302, 1293, 1237, 1152, 1122, 1087, 973, 926, 870, 790, 770, 745, 688 cm-1.

* * * * *

UNITED STATES PATENT AND TRADEMARK OFFICE
CERTIFICATE OF CORRECTION

PATENT NO.       : 8,426,612 B2
APPLICATION NO. : 12/995390
DATED            : April 23, 2013
INVENTOR(S)      : Serafini et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 62 days.

Signed and Sealed this
Eighth Day of September, 2015

Michelle K. Lee
*Director of the United States Patent and Trademark Office*